United States Patent [19]
Houghton

[11] Patent Number: 5,717,104
[45] Date of Patent: Feb. 10, 1998

[54] PROCESS FOR PREPARING INDOLE DERIVATIVES CONTAINING A 1,2,4-TRIAZOL-1-YL SUBSTITUENT

[75] Inventor: Peter Grenville Houghton, Bassingbourn, Great Britain

[73] Assignee: Merck, Sharp & Dohme, Ltd., Hoddesdon, England

[21] Appl. No.: 651,011

[22] Filed: May 20, 1996

Related U.S. Application Data

[62] Division of Ser. No. 373,288, filed as PCT/GB93/01493 Jul. 15, 1993, Pat. No. 5,567,819.

[30] Foreign Application Priority Data

Jul. 22, 1992 [GB] United Kingdom .................. 9215526

[51] Int. Cl.$^6$ ................................................. C07D 249/12
[52] U.S. Cl. ................................................. 548/267.2
[58] Field of Search ........................................ 548/267.2

[56] References Cited

FOREIGN PATENT DOCUMENTS 313397  4/1989  European Pat. Off. .
497512  5/1992  European Pat. Off. .

OTHER PUBLICATIONS

Cram a Hammond, "Organic Chemistry"; 2nd Ed. pp. 565–567, (1964).

Eur. J. Med. Chem., vol. 24 (1989) 537–540, "Synthesis and Antimycotic Activty of New (1H–1,2, 4–triazol–1–yl–methyl) benezeneamine derivatives" by M. Scalzo et al.

*Primary Examiner*—Patricia L. Morris
*Attorney, Agent, or Firm*—Robert J. North; Melvin Winokur

[57] ABSTRACT

A process for preparing tryptamine derivatives and related compounds having a 1,2,4-triazol-1-yl moiety within the molecule comprises reacting 4-amino-1,2,4-triazol with a nitrobenzene derivative containing a readily displaceable group; deaminating the aminotriazolium salt thereby obtained by treatment with nitrous acid followed by neutralisation; reducing the triazolyl-ni-trobenzene derivative thereby obtained by transfer hydrogenation; treating the triazolyl-aniline derivative thereby obtained with nitrous acid and then with an alkali metal sulphate, followed by acidification; and subsequently reacting the triazolyl-hydrazine derivative thereby obtained in situ with a suitable carbonyl compound, to obtain the required triazolyl-indole derivative.

4 Claims, No Drawings

PROCESS FOR PREPARING INDOLE DERIVATIVES CONTAINING A 1,2,4-TRIAZOL-1-YL SUBSTITUENT

This is a division of application Ser. No. 08/373,288 filed Jan. 20, 1995 now U.S. Pat. No. 5,567,819, Ser. No. 07/373,288, now U.S. Pat. No. 5,567,819, is the national stage application filed under 35 USC 371 of international application PCT/93/01493 for continuty purposes.

The present invention relates to the preparation of a class of therapeutically active compounds. More particularly, the invention concerns an improved process for producing tryptamine derivatives and related compounds wherein the molecule also contains a 1,2,4-triazol-1-yl moiety.

EP-A-0497512, published on 5th Aug. 1992, describes inter alia a family of 1,2,4-triazol-1-yl derivatives to which is attached a substituent incorporating a tryptamine or similar moiety. These compounds are stated to be selective agonists of so-called "5-HT$_1$-like" receptors and hence to be of particular use in the treatment of migraine and associated conditions such as cluster headache, chronic paroxysmal hemicrania, headache associated with vascular disorders, tension headache and paediatric migraine.

We have now found an efficient and cost-effective method for preparing the aforementioned family of compounds.

The present invention accordingly provides a process for the preparation of a compound of formula I:

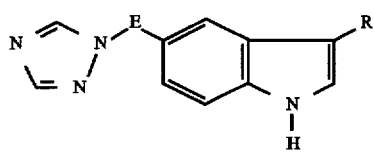

wherein E represents a bond or a straight or branched alkylene chain containing from 1 to 4 carbon atoms; and R represents —CH$_2$.CHR$^1$.NR$^2$R$^3$ or a group of formula

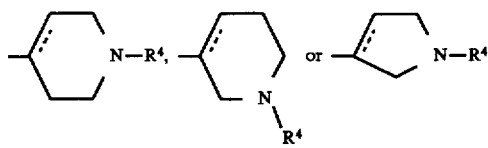

in which the broken line represents an optional chemical bond; and R$^1$ R$^2$ R$^3$ and R$^4$ independently represent hydrogen or C$_{1-6}$ alkyl; which process comprises the following steps:

(i) reaction of 4-amino-1,2,4-triazole of formula II with a compound of formula III:

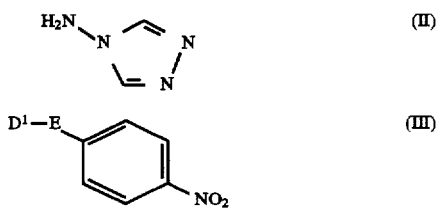

wherein E is as defined above, and D$^1$ represents a readily displaceable group; to obtain a compound of formula IV:

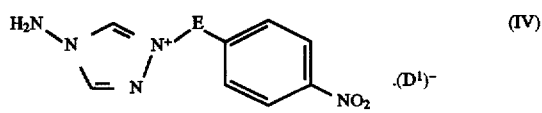

where E and D$^1$ are as defined above;

(ii) deamination of the aminotriazolium salt of formula IV thereby obtained by treatment with nitrous acid followed by neutralisation, to obtain a compound of formula V:

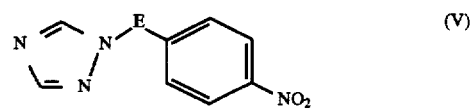

wherein E is as defined above;

(iii) reduction of the nitro compound of formula V thereby obtained by transfer hydrogenation using a hydrogenation catalyst in the presence of a hydrogen donor, to obtain a compound of formula VI:

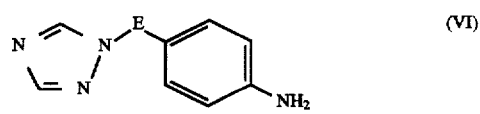

wherein E is as defined above; and (iv) treatment of the aniline derivative of formula VI thereby obtained with nitrous acid and then with an alkali metal sulphite, followed by acidification, to obtain a hydrazine derivative of formula VII:

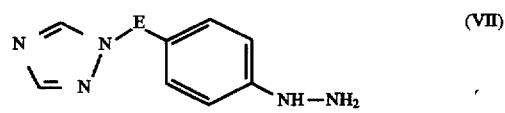

wherein E is as defined above; which compound is subsequently reacted in situ with a compound of formula VIII or a carbonyl-protected form thereof:

wherein R$^a$ corresponds to the group R as defined above or represents a protected derivative thereof, or R$^a$ represents a group of formula —CH$_2$.CHR$^1$D$^2$ in which R$^1$ is as defined above and D$^2$ represents a readily displaceable group; followed, as necessary, by removal of any protecting groups present.

Preferred values for the groups R$^1$, R$^2$, R$^3$ and R$^4$ include hydrogen and methyl. Thus, representative values of R include aminoethyl, N-methylaminoethyl, N,N-dimethylaminoethyl, 4-piperidyl, 1-methyl-4-piperidyl, 3-pyrrolidinyl and 1-methyl-3-pyrrolidinyl. Preferably, R represents N,N-dimethylaminoethyl.

The alkylene chain E may be, for example, methylene, ethylene, 1-methylethylene, propylene or 2-methylpropylene. Alternatively, the group E may represent a single bond such that the nitrogen atom in the 1-position of the 1,2,4-triazol-1-yl moiety is attached directly to the 5-position of the indole nucleus as depicted in formula I, or to the corresponding position in the precursors thereto. Preferably, E represents a methylene linkage.

The readily displaceable group D$^1$ in the compounds of formula III is suitably a halogen atom, preferably bromine; except when the moiety D$^1$ is attached directly to the aromatic ring, i.e. when E represents a bond, in which case D$^1$ is preferably fluorine.

Suitable carbonyl-protected forms of the compounds of formula VIII include the dimethyl acetal derivatives.

The readily displaceable group $D^2$ in the compounds of formula VIII suitably represents a halogen atom, preferably chlorine. When the moiety $R^a$ in the compounds of formula VIII is a group of formula —$CH_2.CHR^1D^2$ the substituent $D^2$ is displaced in situ under the prevailing reaction conditions to afford a final product of formula I wherein R represents a group of formula —$CH_2.CHR^1.NH_2$. The terminal amino group can subsequently, if desired, be further elaborated using techniques known from the art to give a compound of formula I wherein R represents the required group of formula —$CH_2.CHR^1.NR^2R^3$ in which one or both of $R^2$ and $R^3$ is other than hydrogen.

Where $R^a$ in formula VIII represents a protected derivative of the group R, the protecting group employed will suitably be any protecting group known from the art for the required purpose. Examples of suitable protecting groups, together with convenient procedures for their subsequent removal, are described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. A typical-protecting group for a nitrogen atom is the t-butoxycarbonyl (BOC) group, which can be removed at a convenient subsequent stage by treatment with trifluoroacetic acid.

Steps (i) and (ii) of the above-described process comprise the alkylation of 4-amino-1,2,4-triazole at the 1-position, followed by deamination of the resulting aminotriazolium salt by treatment with nitrous acid and subsequent neutralisation. The overall transformation is conveniently effected using reaction conditions analogous to those described in *J. Org. Chem.*, 1989, 54, 731. Thus, step (i) is suitably carried out by heating together the reactants at reflux in an appropriate solvent, preferably a polar solvent such as acetonitrile or a lower alkanol, e.g. isopropyl alcohol, for a time of between 1 and 10 hours, optionally about 7.5 hours. The nitrous acid employed in step (ii) is advantageously generated in situ by mixing sodium nitrite with a mineral acid such as concentrated hydrochloric acid, ideally maintaining the temperature at between −5° C. and 5° C. and avoiding too large an excess of nitrous acid. After an appropriate period, typically about 15 minutes, of stirring at below 5° C., the reaction mixture is allowed to warm to room temperature and subsequently neutralised, ideally with aqueous ammonia solution.

The aminotriazolium salt of formula IV may be isolated as such after step (i) of the process according to the invention, in which case steps (i) and (ii) may be carried out independently; or the procedure of step (ii) may be performed in situ on the reaction mixture obtained from step (i) without isolation of the aminotriazolium salt IV. In other words, steps (i) and (ii) may advantageously be combined in a "one-pot" procedure.

In the procedure described in accompanying Example 1, steps (i) and (ii) are carried out separately. Example 2, meanwhile, describes a "one-pot" procedure for preparing the nitro compound of formula V.

The aminotriazolium salt IV has been found to be obtainable from step (i) in yields typically in the region of 95–96%. Step (ii) has been found to afford the nitro compound V in yields typically of the order of 92–97%. Overall, therefore, considering steps (i) and (ii) together under conditions equivalent to those described in the accompanying Examples, combined yields of the nitro compound V in the region of 83–93% may be expected.

In the previously described procedure (see, for instance, Example 5 of EP-A-0497512, Step 1), the nitro compound of formula V as defined above is prepared directly by alkylation, using a reagent corresponding to the compound of formula III as defined above, of the sodium salt of 1,2,4-triazole. However, the yield of this reaction is reported to be a moderate 52%. This may be accounted for by the fact that, when attempts were made to adapt this procedure for application on an industrial scale, the product was observed to be contaminated with significant amounts of the stilbene derivative of formula IX:

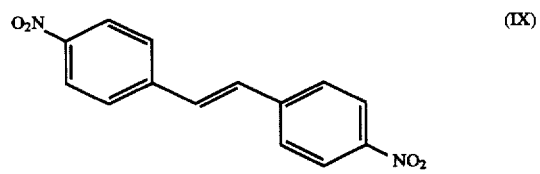

Further attempts to overcome this problem and in fact to improve the procedure generally, by employing 1,2,4-triazole free base in the presence of anhydrous potassium carbonate, had, however, little effect on the efficiency of the process, the desired nitro compound V being obtained in yields of only about 45%. From the above discussion, therefore, it will be apparent that the procedure described in steps (i) and (ii) of the process according to the invention is extremely advantageous in terms of efficiency, since it results in an effective doubling of the yield of product expected therefrom.

The use of 4-amino-1,2,4-triazole II as starting material in the preparation of compounds of formula V has advantages from other viewpoints, also. Firstly, it is an inexpensive reagent, and therefore is beneficial to the overall process from the economic aspect. In addition, the amino functionality in the reagent II directs the course of the reaction such that attack occurs exclusively through the nitrogen atom in the 1-position; it has been observed that the product obtained from the reaction using the sodium salt of 1,2,4-triazole is contaminated with an appreciable amount of the unwanted 1,2,4-triazol-4-yl regioisomer, thereby detrimentally affecting the purity of the product derived therefrom. The fact that a purer product is obtained in effectively double the yield from steps (i) and (ii) of the process according to the invention as compared with the previous procedure also means that recovery and recyclability of the solvent employed is a much more straightforward undertaking.

Steps (i) and (ii) as described above for the preparation of the nitro compounds of formula V is a novel process in its own right, and represents a further feature of the present invention.

Step (iii) of the process according to the present invention comprises the reduction of the nitro compound V to the aniline derivative VI by means of transfer hydrogenation. This procedure employs a hydrogenation catalyst such as palladium on carbon, ideally 10% palladium on carbon, in the presence of a hydrogen donor such as ammonium formate, sodium hypophosphite, triethylammonium formate or potassium formate, preferably ammonium formate. Where ammonium formate is employed as the hydrogen donor, the reaction is conveniently carried out in a solvent such as methanol or ethanol, or aqueous methanol or ethanol. Where methanol or aqueous methanol is employed as the solvent, the reaction is advantageously carried out at a temperature in the region of 35°–45° C. Where ethanol or aqueous ethanol is used, the reaction is suitably carried out at a temperature in the region of 60°–75° C. The time taken for complete reaction will vary depending inter alia upon the temperature of the reaction mixture and upon the amount of hydrogenation catalyst in the reaction mixture. Where a 10% palladium on carbon catalyst is employed, this catalyst will typically be present in an amount of approximately 1% to 4%, ideally 2% to 3.5%, by weight of the nitro compound of formula V, in which case a reaction time of approximately 2 hours will typically be required if the combinations of solvent and reaction temperature illustrated above are utilised. Where appropriate, further aliquots of the hydrogenation catalyst may be added to the reaction mixture periodically, in order to ensure that the reaction proceeds to completion. Under these conditions, an essentially quantitative yield of the aniline derivative VI can be expected to be obtained.

In the previously described procedure (see, for instance, Example 5 of EP-A-0497512, Step 2), reduction of the nitro compound of formula V as defined above to the aniline derivative of formula VI as defined above was effected by way of conventional catalytic hydrogenation. Whilst quantitative yields of the desired product were reportedly obtained, this procedure is nevertheless subject to the practical drawback that it must be performed in an autoclave, which means that it is not readily amenable to scaling up for application on an industrial scale. The transfer hydrogenation methodology, meanwhile, does not require specialised items of laboratory equipment, being readily adaptable for performance in any standard laboratory vessel of unrestricted size, and is accordingly a much more versatile procedure than conventional catalytic hydrogenation from a manufacturing viewpoint.

The procedure described in Step (iii) of the process according to the invention also has the advantage of permitting isolation of the free base form of the amine VI. This is a stable compound. By contrast, the previously described procedure gives rise to the hydrochloride salt. Not only does this result in variability of the product, since mixtures of the mono- and dihydrochloride, etc., salts are obtained in practice, but it is also observed that these hydrochloride salts are light-sensitive; the practical effect of this is that the product obtained is observed to darken in colour with age, which is plainly an undesirable phenomenon.

In step (iv) of the process according to the invention, the aniline derivative VI is first converted into the hydrazine derivative of formula VII by treatment with nitrous acid and then with an alkali metal sulphite, followed by acidification. Without isolating the hydrazine derivative VII, this compound is then reacted in situ with the aldehyde VIII or a carbonyl-protected form thereof, typically the dimethyl acetal derivative, to afford the desired triazolyl-substituted indole of formula I.

As in step (ii) above, the nitrous acid employed in step (iv) is advantageously generated in situ by mixing sodium nitrite with a mineral acid such as concentrated hydrochloric acid, ideally maintaining the temperature this time at between 0° C. and 5° C. and avoiding too large an excess of nitrous acid.

The diazonium salt thereby obtained is then reduced in situ to the hydrazine derivative VII by treatment with an alkali metal sulphite, suitably with gradual heating of the reaction mixture, followed by acidification, ideally with sulphuric acid. The alkali metal sulphite employed is suitably sodium sulphite or potassium sulphite, preferably sodium sulphite.

In the previously described procedure (see, for instance, Example 5 of EP-A-0497512, Step 3), the diazonium salt, obtained upon nitrous acid treatment of the aniline derivative of formula VI as defined above, was reduced to the hydrazine VII by reaction with $SnCl_2$ dihydrate in concentrated HCl. However, tin salts are notoriously toxic, giving rise to significant disposal problems, and the replacement of $SnCl_2$ by sodium sulphite is therefore plainly beneficial from the environmental viewpoint, especially when the process is adapted for full-scale manufacture. Moreover, tin salts are persistent, and trace amounts thereof are frequently observed to be carried through to the final stages of the synthetic sequence unless rigorous chromatography is undertaken; the replacement of $SnCl_2$ by sodium sulphite clearly also removes this drawback.

The reaction between compounds VII and VIII is an example of the well-known Fischer indole synthesis. The reaction proceeds by way of an initial non-cyclised intermediate of formula X:

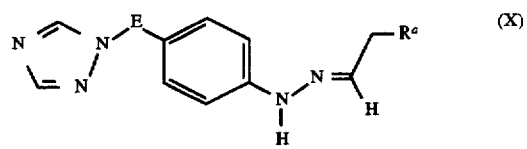

wherein E and $R^a$ are as defined above. However, by judicious choice of reaction conditions, generally by carrying out the reaction at a high enough temperature, the isolation of intermediate X can be avoided. The reaction is advantageously carried out by stirring the reactants in the presence of 4% sulphuric acid at an elevated temperature, typically about 90° C.

A notable advantage associated with the fact that stage (iv) of the process according to the invention is carried out in a single step without isolation of any intermediates is concerned with the difficulty of isolation of the hydrazine derivatives of formula VII. Generally, the hydrazine VII is extremely water soluble, and consequently requires exhaustive extraction before realistic yields thereof can be obtained. This may explain in part the moderate quoted yield (56%) of the hydrazine derivative of formula VII as defined above obtained when this compound was isolated and purified according to the previously described procedure (cf. Example 5 of EP-A-0497512, Step 3).

As with that of the amine VI the hydrochloride salt of the hydrazine derivative VII has been found to be light-sensitive and also to exist as variable mixtures of the mono- and dihydrochloride, etc., salts, thereby emphasising the advisability of avoiding the isolation of the hydrazine derivative VII.

According to the previously described process (cf. EP-A-0497512, Examples 5 and 17), whereby a compound corresponding to formula I as defined above is obtained from the amine of formula VI as defined above by a multi-stage procedure, the overall yield from the amine VI can be calculated to be of the order of 10–20%. Now by utilising the method described in step (iv) of the process according to the present invention, whereby the amino derivative VI is converted in situ directly to the required product of formula I, the overall yield from the amine VI is routinely found to be in the region of 40–45%. This again demonstrates the superiority of the process according to the present invention relative to that described previously. Moreover, since all the reaction stages from the amine VI to the final product I are carried out in the same vessel, it has been found that larger batch sizes than hitherto can be employed.

The following non-limiting Examples are intended to illustrate the present invention.

EXAMPLE 1

Step (i): 4-Amino-1-(4-nitrobenzyl)-4H-1,2,4-triazolium bromide (IV; E=$CH_2$, $D^1$=Br)

A mixture of 4-amino-1,2,4-triazole (250 g, 2.976 moles) and 4-nitrobenzyl bromide (ex Janssen, 99%, 617.5 g, 2.83 moles) in isopropyl alcohol (5.66 l) was brought to reflux with stirring. The mixture became a solution and then, almost immediately, the required triazolium salt crystallised out at reflux. The mixture was stirred and heated under reflux for 7.5 hours and then allowed to cool to room temperature overnight. Next day, the mixture was cooled to 0°–5° C., held for 1 hour and the product filtered, washed with a little isopropyl alcohol and then dried, in vacuo at 50° C., to give the title triazolium salt (808 g) in 95% yield as a white solid, m.p. 199° C. (dec.).

Step (ii): 1-(4-Nitrobenzyl)-1,2,4-triazole (V; E=CH$_2$)

A solution of sodium nitrite (206 g, 2.98 moles) in water (840 ml) was added subsurface over 70 minutes to a suspension of the preceding triazolium salt (808 g, 2.69 moles) in water (5.6 l) and conc. hydrochloric acid (505 ml) at 0°–5° C. The pale yellow slurry was stirred at <5° C. for 15 minutes and then allowed to warm to 25° C. over 1 hour. The colourless solution was adjusted to pH 9 by addition of aqueous ammonia solution (380 ml, 18N) maintaining the temperature <30° C. The mixture was cooled to 0°–5° C. and stirred for 1 hour. The solid was collected by filtration, washed with water (400 ml) containing aqueous ammonium hydroxide (20 ml, 18N) and dried under reduced pressure at 50° C. to give 535 g (97% yield) of the title nitro compound, m.p. 102°–103° C.

Step (iii): 1-(4-Aminobenzyl)-1,2,4-triazole (VI; E=CH$_2$)

The preceding nitro compound (803 g, 3.9, moles), ammonium formate (1.16 kg, 18.4 moles) and 10% Pd/C (28 g) in methanol (8 l) was stirred under a nitrogen atmosphere and warmed to 30° C. Heating was discontinued-and cooling applied to control the exothermic reaction by maintaining the temperature at 35°–5° C. for 2 hours. The reaction mixture was cooled at 20° C. and the catalyst removed by filtration through Hyflo filter aid. The filter pad was washed with methanol (2 l). The filtrate was concentrated and the residue diluted with ethyl acetate (12 l) and water (1.57 l). The lower aqueous layer was treated with aqueous ammonium hydroxide solution (10 ml, 18N) to pH 9. The aqueous layer was separated and extracted with ethyl acetate (2x6 l and 3 l). The combined extract was washed with saturated aqueous sodium hydrogen carbonate solution (1.57 l), dried and evaporated under reduced pressure to give 679 g (99% yield) of the title amine, m.p. 127°–128° C.

Step (iv): N,N-Dimethyl-2-[5-(1,2,4-triazol-1-ylmethyl)-1H-indol-3-yl] ethylamine (I; E=CH$_2$, R=—CH$_2$.CH$_2$.NMe$_2$)

A solution of sodium nitrite (16.7 g, 0.24 mole) in water (22.7 ml) was added subsurface to a solution of the preceding amine (40 g, 0.23 mole) in hydrochloric acid (65.3 ml) and water (162 ml) maintaining the temperature <5° C. The solution was stirred at 0°–5° C. for 1 hour. The solution was added to a suspension of sodium sulphite (72.4 g, 0.57 mole) in water (227 ml) cooled at 5°–10° C. under a nitrogen atmosphere. The red solution was stirred at 5°–10° C. for 10 minutes, allowed to warm to 20° C. over 20 minutes and then heated to 70° C. over 45 minutes. The solution was stirred at 70° C. for 2.5 hours and cooled to 65° C. Concentrated sulphuric acid (56.8 ml) was added to the solution over 15 minutes maintaining the temperature at 70°–80° C. The solution was stirred at 70° C. under a nitrogen atmosphere for 2 hours and then allowed to cool to 20° C. overnight. The solution of the resulting hydrazine (VII; E=CH$_2$) was warmed to 25° C. and 4-(N,N-dimethylamino)-1,1-dimethoxybutane (44.3 g, 0.28 mole) was added over 15 minutes maintaining the temperature <35° C. The solution was stirred at 30°–35° C. for 30 minutes. The mixture was heated to 90° C. over 30 minutes and maintained at 90°–93° C. for 15 minutes. The mixture was cooled to 15° C. and Hyflo filter aid (68 g) added followed by aqueous ammonium hydroxide (200 ml, 18N) to adjust the pH to 11–12. The mixture was filtered and the filtrate and the Hyflo extracted with ethyl acetate (5x300 ml). The extract was dried (Na$_2$SO$_4$) and evaporated under reduced pressure. The residue was chromatographed on silica (550 g) with ethyl acetate:methanol (80:20) changing to ethyl acetate:methanol (50:50). The fractions containing product were evaporated under reduced pressure to give 27.8 g (45% yield) of the title compound in free base form.

EXAMPLE 2

Step (i): "One-pot" preparation of 1-(4-nitrobenzyl)-1,2,4-triazole (V; E=CH$_2$)

4-Nitrobenzyl bromide (64.22 g), 4-amino-1,2,4-triazole (26 g) and isopropyl alcohol (586 ml) were stirred together at reflux for 7% hours. The isopropanol solvent was replaced with water by using an azeotropic distillation procedure, in vacuo, on a Buchi rotary evaporator. The volume of the final aqueous slurry was 750 ml. 675 ml of this slurry was cooled to −2° C. and hydrochloric acid (50.8 ml, 12M) added over a few minutes. A solution of sodium nitrite (21.7 g) in water (86 ml) was then added dropwise, and subsurface over a 40 minute period. The temperature of the batch was kept between −2 and −1° C. during the addition and then allowed to warm to 18° C. over 30 minutes. The temperature was then increased to 28° C. and held for 1 hour and the solution treated with charcoal (4.5 g, Fisons) for 15 minutes. The charcoal was removed and the filtrate (750 ml) divided equally in two. One half of the solution was made basic with ammonia solution (22 ml) and the precipitated base collected, washed with water (2x30 ml) and dried (16 hours at 35° C. in vacuo). This gave an 83.3% yield (22.73 g) of 1-(4-nitrobenzyl)-1,2,4-triazole.

Step (ii): 1-(4-Aminobenzyl)-1,2,4-triazole (VI; E=CH$_2$)

A stainless steel vessel was inerted with nitrogen and connected via its vent to a mobile scrubber unit. The scrubber was charged with very dilute hydrochloric acid. The vessel was charged with 96% ethanol (40 kg) followed by 1-(4-nitrobenzyl)-1,2,4-triazole (9.62 kg). The vessel was re-inerted with nitrogen and a slurry of 10% Pd/c catalyst (Engelhardt type 4505, 192 g) in water added to the stirred batch via the addition funnel. The vessel, funnel and line were rinsed with water. Total water used was 16 l. The batch was well stirred and heated to 60° C. A solution of ammonium formate (13.95 kg) in water (3 l) was metered into the reactor over 1 hour. Batch temperature settled at 65° C. At the end of this addition, the batch was heated at 70°–75° C. for a further 1 hour. Tlc showed complete reaction and single spot formation. The batch was cooled to 60° C. and passed through a pressure filter coated with hyflo (1.5 kg) to another vessel. The reaction vessel, filter and lines were washed with water (10 l). A further batch of 1-(4-nitrobenzyl)-1,2,4-triazole (9.585 kg) was then reduced in the same way. This batch was filtered and added to the previously filtered batch together with a 10 l water wash of the vessel, filter and lines. The combined, filtered batch (215 l) was distilled at atmospheric pressure until 70 l of distillate had been removed (vapour temperature was 83° C. at this point). Water (30 l) was added and the distillation continued until the vapour temperature reached 95° C. (106 l total distillate). The pressure in the distillation vessel was then reduced to allow distillation at a boiling point of ≦70° C. A further 70 l of distillate was removed to leave a residual volume of 69 l. The batch had crystallised at this point and the slurry was cooled to ≦20° C. over 1 hour. The batch was gently stirred and aged overnight. The batch was cooled to 0° C., aged for 1 hour and then filtered. The solid was washed with water at 0°–5° C. (10 l). The batch was dried overnight at 50° C., in vacuo with a nitrogen bleed to give 1-(4-aminobenzyl)-1,2,4-triazole in 96% yield.

I claim:

1. A process for the preparation of a compound of formula V:

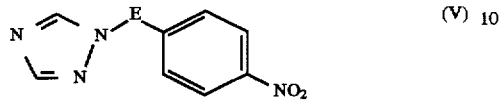 (V)

wherein E represents a bond or a straight or branched alkylene chain containing from 1 to 4 carbon atoms; which process comprises the following steps:

(i) reaction of 4-amino-1,2,4-triazole of formula II with a compound of formula III:

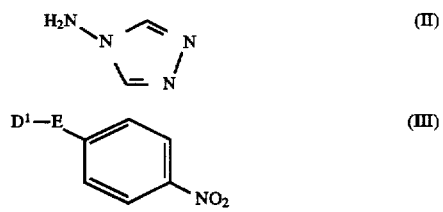

wherein E is as defined above, and $D^1$ represents a readily displaceable group, being a halogen atom; in isopropyl alcohol; to obtain a compound of formula IV:

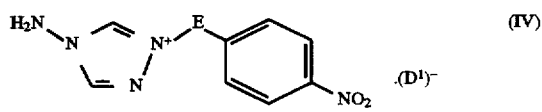 (IV)

where E and $D^1$ are as defined above; and (ii) deamination of the aminotriazolium salt of formula IV thereby obtained by treatment with nitrous acid followed by neutralisation, to obtain the required compound of formula V:

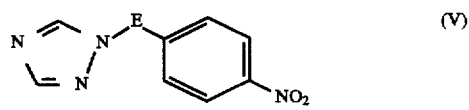 (V)

wherein E is as defined above.

2. A process as claimed in claim 1 wherein E represents a methylene linkage.

3. A process as claimed in claim 1 wherein steps (i) and (ii) are carried out independently, whereby the aminotriazolium salt of formula IV is isolated as such after step (i).

4. A process as claimed in claim 1 wherein the procedure of step (ii) is performed in situ on the reaction mixture obtained from step (i) without isolation of the aminotriazolium salt IV, whereby steps (i) and (ii) are combined in a "one-pot" procedure.

* * * * *